United States Patent [19]

Hulsmann et al.

[11] 4,112,240
[45] Sep. 5, 1978

[54] PROCESS FOR THE MANUFACTURE OF LIGHT COLORED DIPROPYLENEGLYCOL DIBENZOATE

[75] Inventors: Hans Leo Hulsmann, Wetter, Ruhr; Gustav Renckhoff, Witten, Ruhr, both of Fed. Rep. of Germany

[73] Assignee: Dynamit Nobel Aktiengesellschaft, Troisdorf, Bezirk Cologne, Fed. Rep. of Germany

[21] Appl. No.: 712,580

[22] Filed: Aug. 9, 1976

Related U.S. Application Data

[63] Continuation of Ser. No. 505,113, Sep. 11, 1974, abandoned.

[30] Foreign Application Priority Data

Sep. 15, 1973 [DE] Fed. Rep. of Germany ....... 2346560

[51] Int. Cl.² .............................................. C07C 69/78
[52] U.S. Cl. ......................................... 560/112; 560/77
[58] Field of Search ...................... 260/476 R; 560/112

[56] References Cited

U.S. PATENT DOCUMENTS

| | | | |
|---|---|---|---|
| 2,822,348 | 2/1958 | Haslam ................................... 260/75 |
| 3,031,491 | 4/1962 | Dobson et al. ....................... 260/475 |
| 3,098,093 | 7/1963 | Hagemeyer et al. ............. 260/476 R |
| 3,194,791 | 7/1965 | Wilson et al. .......................... 260/75 |
| 3,356,712 | 12/1967 | Renckhoff et al. ............... 260/476 R |
| 3,696,141 | 10/1972 | Hulsmann et al. .................. 260/476 |
| 3,784,578 | 1/1974 | Swodenk et al. ................. 260/476 R |

OTHER PUBLICATIONS

Wilfong, J. Polymer Science, 54, pp. 388–389 (1961).

*Primary Examiner*—Jane S. Myers
*Attorney, Agent, or Firm*—Burgess, Dinklage & Sprung

[57] ABSTRACT

Process for production of dipropyleneglycol dibenzoate isomer mixture of the formulas:

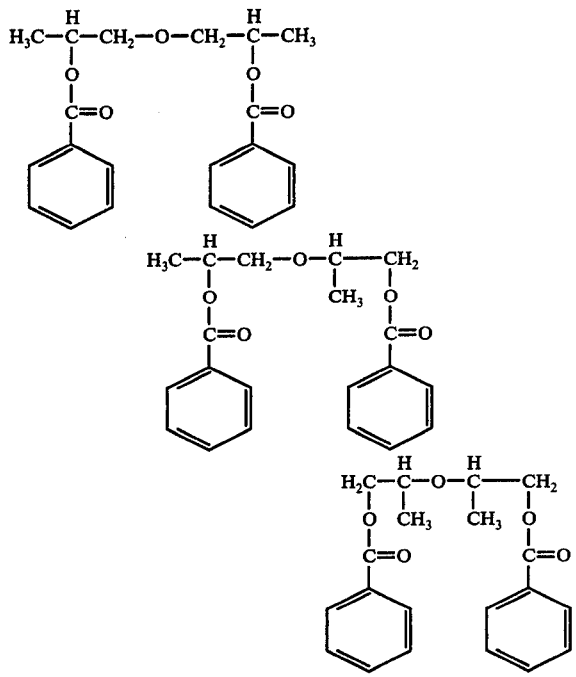

A crude methyl benzoate containing at least 80 wt.% methylbenzoate, which is a by-product of production of dimethylterephthalate by catalytic oxidation of p-xylene and/or methyl-p-toluate and esterification of the resulting acids with methanol, is contacted with dipropylene glycol commercial isomer mixture in the presence of a catalyst for a transesterification to produce said benzoate. The catalyst is an aluminum alkoxide or an aluminum silicon alkoxide containing the group Al O Si. The product is obtained in good yield, has good color, and is useful as a plasticizer for PVC.

6 Claims, No Drawings

PROCESS FOR THE MANUFACTURE OF LIGHT COLORED DIPROPYLENEGLYCOL DIBENZOATE

This is a continuation of application Ser. No. 505,113 filed Sept. 11, 1974, now abandoned.

BACKGROUND

The subject matter of the invention is a process for the manufacture of light colored dipropyleneglycol dibenzoate from the by-products produced in the large-scale production of dimethylterephthalate by the method of the catalytic air oxidation of p-xylene and/or methyl-p-toluate, esterification of the oxidates with methanol, and separation of the esters.

After the esterification with methanol of the acids formed in the air oxidation of p-xylene, the methyl esters — mainly methyl-p-toluate, dimethylterephthalate and methyl esters of other mono- and polyfunctional acids — are separated from one another by distillation or recrystallization or by a method combining these two steps. Dimethylterephthalate is obtained, useful intermediates are recycled into the process, and by-products are purged off. The by-products consist in part of methyl benzoate, which is accompanied by a number of compounds having nearly equal boiling points. Without the previous removal of these compounds whose boiling points are so close to that of methyl benzoate — e.g., by an oxidative preliminary treatment in accordance with the method of German "Auslegeschrift" No. 1,927,544 — the recovery of pure methyl benzoate is impossible, even with expensive distillation processes. The methyl benzoate produced in large plants from the production of dimethylterephthalate usually has a methyl benzoate content in excess of 80%.

Now, if an attempt is made to transesterify such a technical methyl benzoate containing at least 80% of this ester, which has not been pre-treated, with dipropylene glycol isomer mixture consisting of 1,1'-oxy-di-2-propanol, 2-(hydroxypropoxy)-1-propanol and 2,2'-oxy-di-1-propanol in the presence of known transesterification catalysts, it is found that some of the latter, such as antimony trioxide and boron trioxide for example, are unexpectedly completely inactive, and others, such as sodium methylate, catalyze the reaction sluggishly, indicating the formation of inhibitive substances from the substances accompanying the methyl benzoate. A number of other transesterification catalysts, such as tetrabutyl titanate, zinc compounds and magnesium compounds, are sufficiently active, but the color of the esters obtained is brown to brownish black. Iodine color numbers as high as 150 occur. In many cases the esters are so brown and even black that measurement of the iodine color numbers is not possible. A number of examples are listed in Table 1. This table shows the iodine color numbers obtained in the transesterification products of technical methyl benzoate and dipropylene glycol in identical standard batches and under comparable conditions, using a variety of catalysts. The examples are selected so as to present end products of an approximately equal degree of transesterification as indicated by their hydroxyl numbers ranging from 10 to 30.

Table 1

| Catalyst | Amount of Catalyst (%) | Transesterification Time (Hours) | Hydroxyl Number | Iodine Color Number |
|---|---|---|---|---|
| Sodium ethylate | 0.2 | 11 | 24 | 100 |
| Magnesium acetate | 0.2 | 5 | 30 | 80 |
| Magnesium methylate | 0.2 | 3 | 19 | 130 |
| Zinc stearate | 0.2 | 7 | 13 | 100 |
| Zinc dust | 0.2 | 3 | 18 | 30 |
| Dibutyl tin laureate | 0.2 | 4 | 17 | 70 |
| Tin (IV) butylate | 0.2 | 4 | blackish | brown |
| Titanium-silicon alkoxide | 0.2 | 4 | blackish | brown |
| Glycerin titanate | 0.2 | 8 | 17 | 80 |
| Tetrabutyl titanate | 0.2 | 2 | 27 | 60 |
| Tetrabutyl titanate | 0.1 | 4 | 30 | 60 |
| Tetrabutyl titanate | 0.5 | 2 | 20 | 70 |

The dark color of the esters cannot be lightened substantially by means of bleaching agents such as active charcoal or bleaching earths. Oxidants such as hydrogen peroxide or ozone also produce no definite effect. Vacuum distillation yields dark yellow distillates, but the color quality is not adequate for technical use. In addition, thermolysis of the ester takes place at the high temperatures that are used, with a yielding of benzoic acid, resulting in acidity in the distillates, reductions of yield and considerable technical difficulty due to the production of sublimates in the apparatus.

The methyl benzoate that is produced in considerable quantities as a technical by-product has therefore been unable to be used for the production of light colored transesterification products.

THE INVENTION

Surprisingly it has been found that light colored dipropyleneglycol dibenzoate isomer mixture can be produced by esterifying at temperatures above 150° C, preferably by an inert atmosphere, impure methyl benzoate, especially methyl benzoate produced as a by-product in the production of dimethylterephthalate from p-xylene and/or methyl-p-toluate by catalytic air oxidation, e.g., in accordance with DBP 1,041,145, containing over 80 wt-% methylbenzoate, with dipropylene glycol commercial isomer mixture in the presence of aluminum alkoxides and/or aluminum silicon alkoxides which contain the group ALOSi in the nucleus and whose alkoxy group contains identical or different alkoxy radicals of 1 to 4 carbon atoms, such as aluminum ethylate, aluminum-n-propylate, aluminum-sec.-butylate or $(C_2H_5O)_3SiOAl(OC_4H_9\text{-sec.})_2$, as catalysts, removing the compounds of lower boiling points than dipropylene-glycol dibenzoate by distillation, preferably in vacuo, after the yielding of methanol has ended, ozonizing the transesterification product if necessary for color improvement, after cooling it to less than 150° C, and refining it, if desired, in a conventional manner.

The inert atmosphere is produced by displacing the air by means of gases containing little or no oxygen, such as nitrogen, helium or, in some cases, hydrogen.

The technical methyl benzoate of a purity better than 80% is used in an amount at least equivalent to 2 moles of actual methyl benzoate per mole of dipropylene glycol. A slight excess of up to 25 mole-% methyl benzoate may be beneficial towards a rapid performance of the reaction. If in the large-scale dimethylterephthalate process the methyl benzoate is produced with purities of less than 80% by weight, it is to be concentrated by simple distillation to at least 80% by weight.

The catalyst concentration is best not to exceed 0.8%, but generally amounts to 0.02 to 0.5, preferably 0.05 to 0.2% of the sum of the input weights of methyl benzoate and dipropylene glycol.

When the mixtures are heated, at first small amounts of low-boiling compounds and water distill out. At a vat temperature of about 150° C the evolution of methanol begins. During the transesterification the reaction temperature rises steadily to about 270° C. The transesterification is best performed under an inert gas, such as nitrogen.

When the special catalysts in accordance with the invention are used, the impurities accompanying the methyl benzoate, which in themselves are very reactive, and which otherwise are easily transformed by chemical reactions into dark colored products, as is apparent in Table 1 for example, remain substantially unaltered: hence the light color of transesterification products. On account of the great difference in the boiling points of the impurities and of the dipropyleneglycol dibenzoate, the former may easily be removed after the transesterification has ended, by distillation, preferably in vacuo. If an excess of methyl benzoate has been used, this excess is also removed by distillation. This ester distillate may be added to another batch without impairing the color quality of the final product.

After the "low boilers" have been distilled off, light colored dipropyleneglycol dibenzoate remains. The color can be further lightened, if desired, by treatment, preferably at reduced pressure, with a gas stream containing ozone, in contrast to the finding described before that the dark color of the esters prepared with conventional catalysts is not appreciably improved by oxidents.

If the methyl benzoate used contains small amounts of free acids, the final product will have an acid numbers corresponding thereto. In these cases a deacidifying refinement, like the refinement commonly performed in the production of plasticizers, may be performed at low cost, e.g. by treatment of the dipropylene glycol dibenzoate with aqueous alkaline solutions. Small amounts of easily volatile substances may be removed by blowing them out with air or steam.

Dipropyleneglycol dibenzoate is a high quality, fast setting plasticizer for polymers, such as polyvinyl chloride, for example, and can be used in known conventional ways for that purpose.

Thus, the invention provides a process for the manufacture of dipropyleneglycol dibenzoate, which comprises contacting technical benzoate containing more than 80 wt.% methyl benzoate with dipropyleneglycol in the presence of at least one of aluminum alkoxide and aluminum silicone alkoxide as catalyst, at temperature above 150° C, for a time sufficient for transesterification to produce said dipropyleneglycol dibenzoate.

The technical methyl benzoate is the product of production of dimethylterephthalate by catalytic oxidation of p-xylene and/or methyl-p-toluate and esterification of the resulting acids with methanol, to produce a crude reaction product rich in dimethylterephthalate, treatment of the crude product to recover dimethylterephthalate and produce said technical methyl benzoate as a by-product containing at least 80 wt.% methyl benzoate.

The catalyst can be of the formula:

$Al(OR)_3$ or $(RO)_3SiOAl(OR)_2$ wherein the R's are alike or different and are lower alkyl.

The process of the invention is explained by the following examples:

EXAMPLE 1

In a 10-liter flask with electrical heating, stirrer, a fractioning column with glass Raschig rings and a nitrogen feed, 2144 weight parts of dipropylene glycol (= 16 moles) and 5227 weight parts of technical methyl benzoate with a purity of 93.6 wt-% (= 36 moles of pure ester content) were heated at atmospheric pressure with the addition of 7.4 weight parts of aluminum-sec.-butylate ($Al(OC_4H_9\text{-sec.})_3$) as catalyst (=0.1 wt-% with reference to the sum of the input quantities) as catalyst. At temperatures in the reaction flask up to 160° C, easily volatile compounds and water at first distilled out of the mixture. At 160° C the evolution of methanol began. For 5 hours the flask temperature rose steadily to 240° C. After this time the evolution of methanol had ended. The methanol-containing distillate had a content of 95% as measured by gas chromatography; the rest consisted of substances accompanying the technical methyl benzoate input product. Low-boiling substances and the excess methyl benzoate were then removed by distillation, after cooling, at temperatures up to 200° C in a vacuum of 20 Torr. The dipropyleneglycol dibenzoate obtained in a yield of 98% of the theory with reference to the dipropyleneglycol input had an acid number of 1.6, a saponification number of 326.5 (calculated 328) and an iodine color number of 10. The product was cooled to 150° C and ozonized for 30 minutes (ozone apparatus Model S2 made by Argentox, Hamburg; output: 1.5 g $O_3$ per hour at 12 kV and 90W). After the ozonization the iodine color number was 3, and after aqueous-alkaline refinement it was 2. The acid number of the final product was 0.3, the saponification number 329.5.

EXAMPLE 2

Example 1 was repeated, 5818 weight parts (= 40 moles of pure ester content) of technical methyl benzoate (purity: 93.6 wt-%) being used instead of 5227 weight parts. The transesterification ended in 4 hours under otherwise the same conditions.

EXAMPLE 3

When other catalysts to be used according to the invention were used, the following reaction times and product iodine color numbers resulted under otherwise the same reaction conditions:

Table 2

| Catalyst | Amount (wt-%) | Reaction Time | Iodine Color Number of Final Product |
|---|---|---|---|
| Al-ethylate[1] | 0.05 | 5.5 h | 1 – 2 |
| Al-ethylate[1] | 0.1 | 4 h | 1 – 2 |
| Al-ethylate[1] | 0.2 | 3.5 h | 1 – 2 |
| Al-n-propylate[2] | 0.1 | 4.5 h | 1 – 2 |
| Al-i-propylate[3] | 0.1 | 4 h | 1 – 2 |
| Al-Si-alcoholate[4] | 0.1 | 5 h | 2 |

[1] $Al(OC_2H_5)_3$
[2] $Al(OC_3H_7)_3$
[3] $Al(OC_3H_7\text{-i})_3$
[4] $(C_2H_5O)_3SiOAl(OC_4H_9\text{-sec.})_2$

What is claimed is:

1. Process for the manufacture of dipropyleneglycol dibenzoate isomer mixture, which comprises contacting technical methyl benzoate containing more than 80 wt.% methyl benzoate which is the product of production of dimethyl terephthalate by catalytic oxidation of p-xylene and/or methyl-p-toluate and esterification of the resulting acids with methanol, to produce a crude reaction product rich in dimethylterephthalate, treatment of the crude product to recover dimethylterephthalate and produce said technical methyl benzoate as a by-product, with dipropylene glycol commercial isomer mixture of 1,1'-oxy-di-2-propanol, 2-(hydroxypropoxy)-1-propanol, and 2,2''-oxy-di-1-propanol, in the presence of at least one of aluminum and aluminum silicon alkoxides of the formula Al(OR)$_3$ or (RO)$_3$SiOAl(OR)$_2$ wherein the R's are alike or different and are lower alkyl, as catalyst, at temperature above 150° C, for a time sufficient for transesterification to produce said dipropyleneglycol dipropyleneglycol dibenzoate.

2. Process according to claim 1, wherein the transesterification product includes compounds boiling at a lower boiling point than the dipropyleneglycol dibenzoate, said compounds are removed from the transesterification product by distillation, and the dipropyleneglycol dibenzoate resulting from said distillation is connected with ozone at a temperature of less than 150° C and for a time sufficient to improve the color thereof.

3. Process according to claim 1, wherein the amount of catalyst is up to 0.8% of the sum of the input weight of methyl benzoate and dipropylene glycol.

4. Process according to claim 1, wherein said catalyst is at least one of

Al(OC$_2$H$_5$)$_3$

Al(OC$_3$H$_7$)$_3$

Al(OC$_3$H$_7$-i)$_3$ (C$_2$H$_5$O)$_3$Si—O—Al(OC$_4$H$_9$-sec.)$_2$.

5. Process according to claim 1, wherein the catalyst is Al(OR)$_3$.

6. Process according to claim 1, wherein the catalyst is (RO)$_3$ SiOAl(OR)$_2$.

* * * * *

UNITED STATES PATENT AND TRADEMARK OFFICE
CERTIFICATE OF CORRECTION

PATENT NO. : 4,112,240
DATED : September 5, 1978
INVENTOR(S) : Hans Leo Hulsman and Gustav Renckhoff It is certified that error appears in the above-identified patent and that said Letters Patent are hereby corrected as shown below:

Col. 2, line 18, under "Tetrabutyl titanate", delete -- titanate --;

Col. 2, line 40, change "by" to --in--.

Signed and Sealed this

First Day of May 1979

[SEAL]

Attest:

RUTH C. MASON
Attesting Officer

DONALD W. BANNER
Commissioner of Patents and Trademarks